United States Patent
Goshen et al.

(10) Patent No.: US 10,096,120 B2
(45) Date of Patent: Oct. 9, 2018

(54) BONE SEGMENTATION FROM IMAGE DATA

(71) Applicant: KONINKLIJKE PHILIPS N.V., Eindhoven (NL)

(72) Inventors: Liran Goshen, Pardes-Hanna (IL); Asher Gringauz, Nesher (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 18 days.

(21) Appl. No.: 15/101,938

(22) PCT Filed: Dec. 2, 2014

(86) PCT No.: PCT/IB2014/066499
§ 371 (c)(1),
(2) Date: Jun. 6, 2016

(87) PCT Pub. No.: WO2015/083065
PCT Pub. Date: Jun. 11, 2015

(65) Prior Publication Data
US 2016/0307330 A1    Oct. 20, 2016

Related U.S. Application Data

(60) Provisional application No. 61/912,602, filed on Dec. 6, 2013.

(51) Int. Cl.
*G06T 7/143* (2017.01)
*G06T 7/00* (2017.01)
(Continued)

(52) U.S. Cl.
CPC ............ *G06T 7/0087* (2013.01); *G06T 5/002* (2013.01); *G06T 7/11* (2017.01); *G06T 7/143* (2017.01);
(Continued)

(58) Field of Classification Search
CPC ......... G06T 5/002; G06T 7/0087; G06T 7/11; G06T 7/143; G06T 2207/10081;
(Continued)

(56) References Cited

U.S. PATENT DOCUMENTS 7,015,907 B2 * 3/2006 Tek .................... G06T 17/00
345/419
7,856,134 B2 * 12/2010 Ruhrnschopf ......... A61B 6/032
382/128

(Continued)

FOREIGN PATENT DOCUMENTS

JP       3258233      2/2002
WO    2008/078231   7/2008
(Continued)

OTHER PUBLICATIONS

Shi et al., "Normalized cuts and image segmentation," Pattern Analysis and Machine Intelligence, IEEE Transactions on 22.8 (2000): 888-905.
(Continued)

*Primary Examiner* — Mekonen Bekele

(57) ABSTRACT

A method for segmenting bone in spectral image data is described herein. The spectral image data includes at least a first set of image data corresponding to a first energy and second set of image data corresponding to a second different energy. The method includes obtaining the spectral image data. The method further includes extracting a set of features for each voxel in spectral image data. The method further includes determining, for each voxel, a probability that each voxel represents bone structure based on the set of features. The method further includes extracting bone structure from the spectral image data based on the probabilities.

17 Claims, 3 Drawing Sheets

Figure 1:
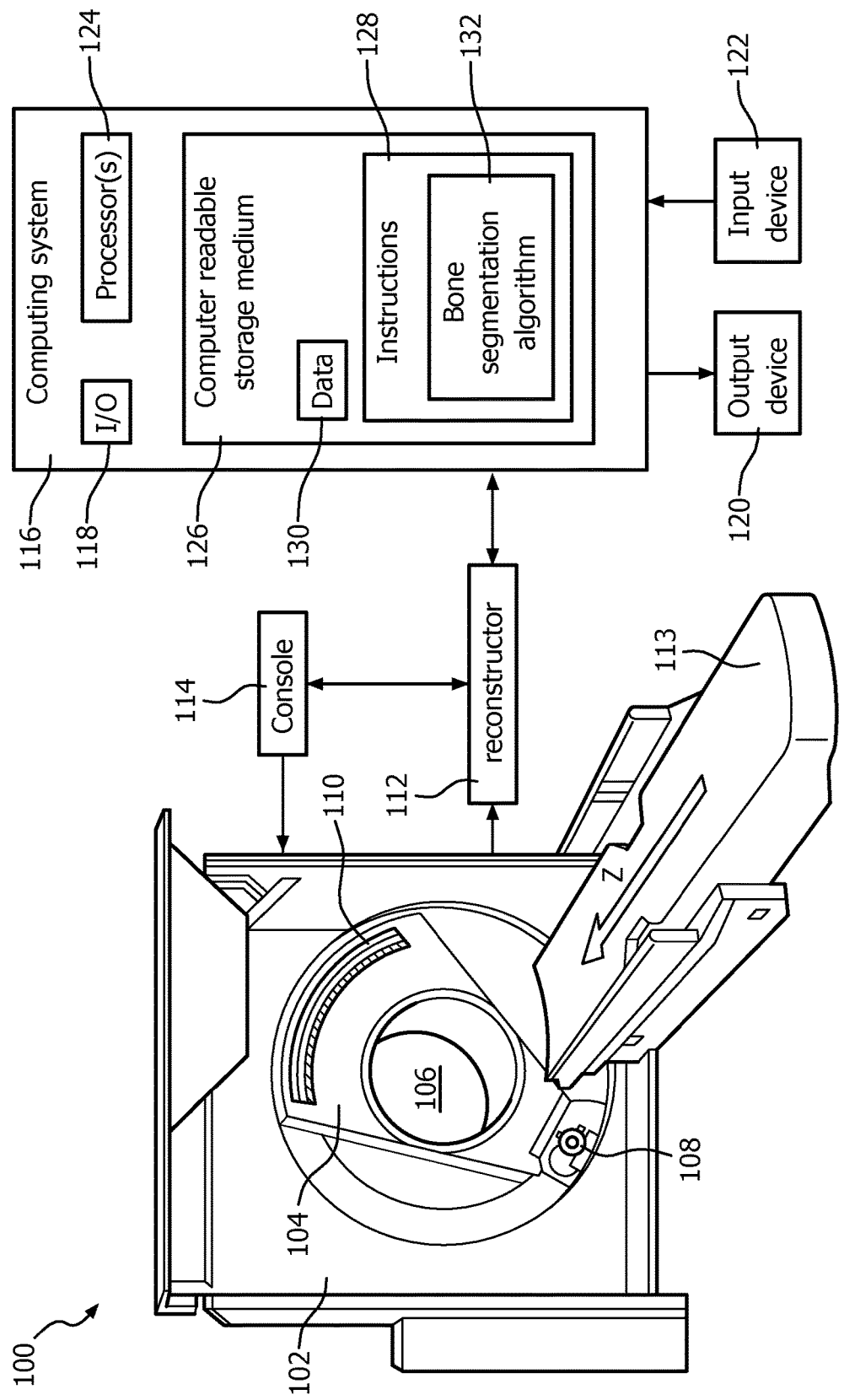

(51) Int. Cl.
  *G06T 5/00*   (2006.01)
  *G06T 7/11*   (2017.01)
  *G06F 19/00*  (2018.01)
(52) U.S. Cl.
  CPC .. *G06F 19/321* (2013.01); *G06T 2207/10081* (2013.01); *G06T 2207/20076* (2013.01); *G06T 2207/30008* (2013.01)
(58) Field of Classification Search
  CPC . G06T 2207/20076; G06T 2207/30008; G06F 19/321
  See application file for complete search history.

(56) References Cited

U.S. PATENT DOCUMENTS

| | | | |
|---|---|---|---|
| 7,968,853 B2 | 6/2011 | Altman | |
| 9,305,351 B2* | 4/2016 | Partain | G06T 7/0014 |
| 9,547,889 B2* | 1/2017 | Goshen | G06T 5/002 |
| 2005/0036691 A1* | 2/2005 | Cathier | G06K 9/4647 |
| | | | 382/203 |
| 2007/0092127 A1 | 4/2007 | Grasruck | |
| 2008/0013672 A1 | 1/2008 | Krauss | |
| 2008/0063135 A1* | 3/2008 | DeMan | A61B 6/032 |
| | | | 378/4 |
| 2008/0253508 A1* | 10/2008 | Krauss | A61B 6/032 |
| | | | 378/19 |
| 2009/0028403 A1* | 1/2009 | Bar-Aviv | G06F 19/321 |
| | | | 382/128 |
| 2009/0153551 A1* | 6/2009 | Park | G06T 19/20 |
| | | | 345/419 |
| 2010/0079630 A1* | 4/2010 | Mishima | H04N 9/045 |
| | | | 348/248 |
| 2010/0328313 A1 | 12/2010 | Zamyatin | |
| 2011/0033099 A1 | 2/2011 | Kadomura | |
| 2011/0103654 A1 | 5/2011 | Lavoie | |
| 2013/0039592 A1 | 2/2013 | Lang | |
| 2014/0133729 A1* | 5/2014 | Goshen | G06T 5/002 |
| | | | 382/131 |
| 2014/0369582 A1* | 12/2014 | Partain | G06T 7/0014 |
| | | | 382/131 |
| 2017/0124686 A1* | 5/2017 | Goshen | G06T 5/002 |

FOREIGN PATENT DOCUMENTS

| | | |
|---|---|---|
| WO | 2013/011418 | 1/2013 |
| WO | 2014/128595 | 8/2014 |

OTHER PUBLICATIONS

Goldstein et al., "Geometric applications of the split Bregman method: segmentation and surface reconstruction," Journal of Scientific Computing 45.1-3 (2010): 272-293.

Choi, et al: "Automated pulmonary nodule detection based on three-dimensional shape-based feature descriptor", Computer Methods and Programs in Biomedicine, vol. 113, No. 1, Sep. 7, 2013.

Tavakoli, et al: "A survey of shaped-based registration and segmentation techniques for cardiac images". Computer Vision and Image Understanding, vol. 117, No. 9, Sep. 1, 2013.

Chan, et al: "Active Contours Without Edges", IEEE Transactions on Image Processing, IEEE Service Center, Piscataway, NJ, US, vol. 10, No. 2, Feb. 1, 2001.

Chan, et al., "Algorithms for Finding Global Minimizers of Image Segmentation and Denoising Models", 2004.

\* cited by examiner

BONE SEGMENTATION FROM IMAGE DATA

CROSS REFERENCE TO RELATED APPLICATIONS

This application is the U.S. National Phase application under 35 U.S.C. § 371 of International Application No. PCTIB2014/066499, filed Dec. 2, 2014, published as WO 2015/083065 on Jun. 11, 2015, which claims the benefit of U.S. Provisional Patent Application No. 61/912,602 filed Dec. 6, 2013. These applications are hereby incorporated by reference herein.

The following generally relates to image data processing and more particularly to bone segmentation from image data, and is described with particular application to computed tomography (CT). However, the following is also amenable to other imaging modalities.

A CT scanner includes an x-ray tube mounted on a rotatable gantry opposite a detector array and across an examination region. The rotatable gantry and the x-ray tube rotate around the examination region. The x-ray tube emits radiation that traverses the examination region and is detected by the detector array. The detector array generates and outputs a signal indicative of the detected radiation. The signal is reconstructed to generate three dimensional volumetric image data. The volumetric image data includes voxels that are represented in terms of gray scale intensity values corresponding to relative radiodensity.

The gray scale values reflect the attenuation characteristics of the scanned subject, and show anatomical structures within the scanned subject. The absorption of a photon by a material is dependent on the energy of the photon traversing the material, thus the detected radiation also includes spectral information, which provides additional information indicative of the elemental or material composition (e.g., atomic number) of the scanned material of the subject and/or object. Unfortunately, conventional CT image data does not reflect the spectral characteristics as the signal output by the detector array is proportional to the energy fluence integrated over the energy spectrum.

Spectral CT captures the above-noted spectral characteristics. Generally, a spectral CT scanner may include multiple x-ray tubes configured to emit radiation having different mean spectrums, a single x-ray tube configured to be controllably switched between at least two different emission voltages (e.g., 80 kVp and 140 kVp) during scanning, a single broad spectrum x-ray tube, and/or an energy-resolving detector array with energy-resolving detectors (e.g., with photon counting detectors, at least two sets of photodiodes with different spectral sensitivities, etc.) and discrimination electronics.

Dual-energy CT utilizes two attenuation values acquired simultaneously at two photon energies to solve the photoelectric and Compton contribution that consists of the mass attenuation coefficient of a material, and thus to identify an unknown material by its value of photoelectric and Compton contribution. Because any two linearly independent sums of two basis functions span the entire attenuation coefficient space, any material can be represented by a linear combination of two other materials, so called basis materials, such as water and iodine.

Clinical applications often require segmentation of bone structures in CT image data. Segmentation approaches, for example, are based on time consuming and tedious semi-automatic methods like atlas based methods followed by interactive editing tools to correct the results or faster methods with no need for interactivity, which lack in precision. In general, simple density or gradient operators do not allow precise and reliable bone segmentation due to the fact that different tissues, e.g. bones and vessels, possess the same density range and may lie in close spatial proximity.

Performing quality bone segmentation, even with spectral CT, is a very challenging task, as the bone has a complex structure and has a heterogeneous material composition. An underlying challenge is that some bone structures have attenuation and spectral characteristic that is very similar to other structures in the body, e.g., contrast enhanced organs. In addition, spectral CT studies suffer from an inherently significant noise issue that further enhances the challenge. As a result, bone segmentation algorithms that are based mostly on spectral information deliver poor results.

Aspects described herein address the above-referenced problems and others.

The following describes a fast, automatic and robust bone segmentation algorithm for spectral CT. The bone segmentation algorithm includes removal of spectral noise with an approach that preserves the underlying object structure and spectral information, followed by extraction of a set of features for each voxel in the dataset, determination of a probability of each voxel belonging to bone structure, segmentation of global structure of bone of the image data, and optional visual enhancement of the segmented bone structure.

In one aspect, a method for segmenting bone in spectral image data is described herein. The spectral image data includes at least a first set of image data corresponding to a first energy and second set of image data corresponding to a second different energy. The method includes obtaining the spectral image data. The method further includes extracting a set of features for each voxel in spectral image data. The method further includes determining, for each voxel, a probability that each voxel represents bone structure based on the set of features. The method further includes extracting bone structure from the spectral image data based on the probabilities.

In another aspect, a computing system includes computer readable storage medium that stores a bone segmentation algorithm and a computer processor that executes the bone segmentation algorithm, which causes the computer processor to: extract bone structure from spectral image data based on a probability that each voxel in the spectral image data represents bone structure.

In another aspect, a computer readable storage medium is encoded with computer readable instructions. The computer readable instructions, when executed by a processer, cause the processor to: obtain spectral image data, wherein the spectral image data includes at least a first set of image data corresponding to a first energy and second set of image data corresponding to a second different energy, de-noise the spectral image data, wherein the set of features is extracted from the de-noised spectral image data, extract a set of features for each voxel in de-noised spectral image data, determine, for each voxel, a probability that each voxel represents bone structure based on the set of features, extract bone structure from the spectral image data based on the probabilities, and visually refine the extracted bone.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with a computing system with a bone segmentation algorithm.

Figure 2:
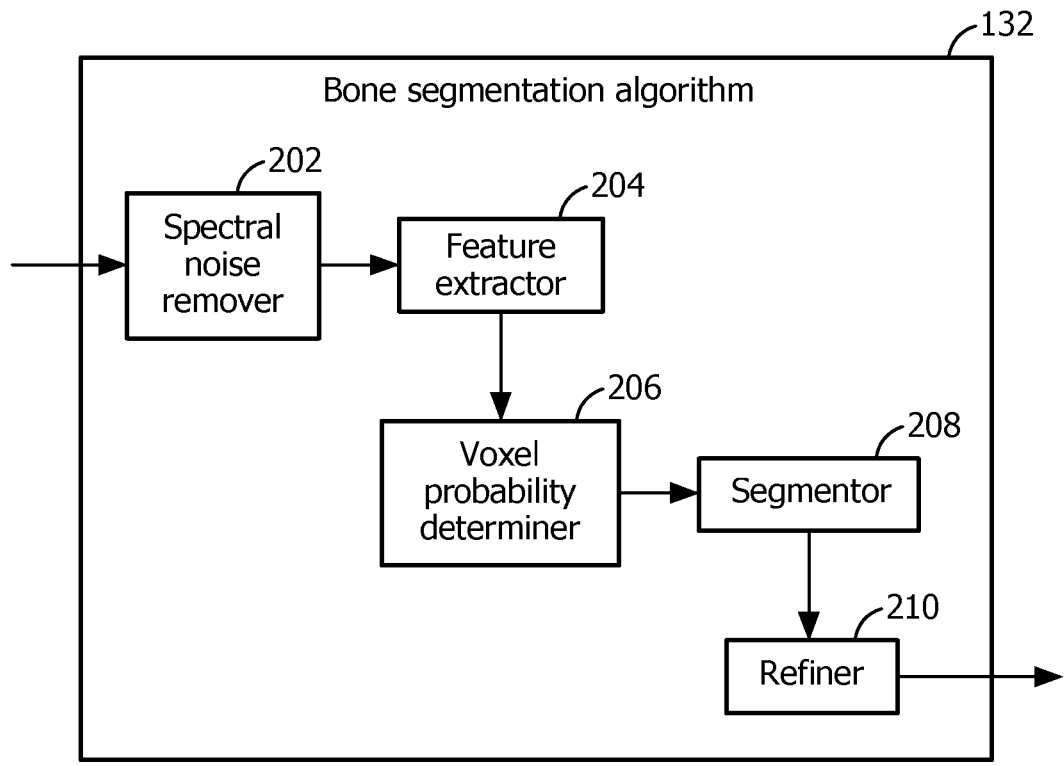

FIG. 2 schematically illustrates an example of the bone segmentation algorithm.

Figure 3:
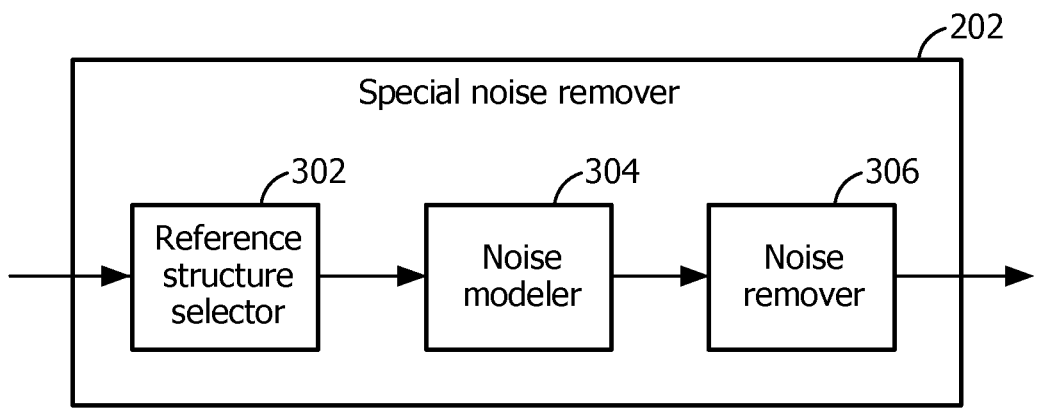

FIG. 3 schematically illustrates an example of the spectral noise remover of the segmentation algorithm.

Figure 4:
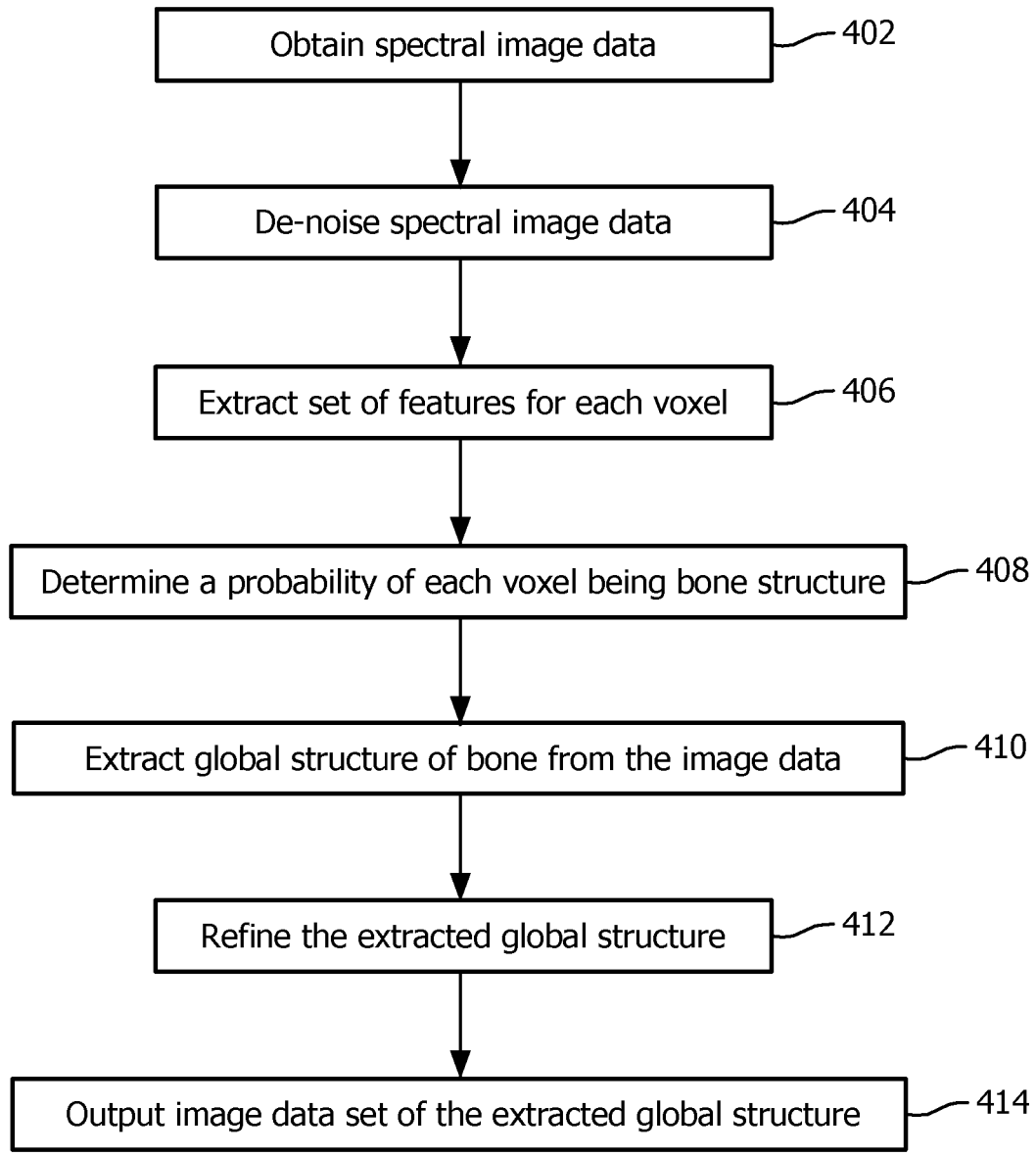

FIG. 4 illustrates an example method for segmenting bone from image data.

FIG. 1 schematically illustrates an imaging system 100 such as a computed tomography (CT) scanner. The imaging system 100 includes a generally stationary gantry 102 and a rotating gantry 104. The rotating gantry 104 is rotatably supported by the stationary gantry 102 and rotates around an examination region 106 about a longitudinal or z-axis ("Z").

A radiation source 108, such as an x-ray tube, is rotatably supported by the rotating gantry 104 and rotates with the rotating gantry 104 and emits poly-energetic radiation that traverses the examination region 106. In the illustrated embodiment, the radiation source 108 includes a single broad spectrum x-ray tube. In a variation, the radiation source 108 is configured to be controllably switched between at least two different emission voltages (e.g., 80 kVp, 140 kVp, etc.) during scanning. In yet another variation, the radiation source 108 includes two or more x-ray tubes configured to emit radiation with different mean spectrums. In another variation, the radiation source 108 includes a combination of the above.

A radiation sensitive detector array 110 subtends an angular arc opposite the radiation source 108 across the examination region 106. The array 110 includes one or more rows of detectors arranged with respect to each other along a z-axis direction, detects radiation traversing the examination region 106, and generates signals indicative thereof. The illustrated array 110 includes a dual-energy detector with at least two scintillators having different x-ray energy sensitivities and at least two corresponding photosensors having corresponding optical sensitivities. An example is described in Ser. No. 11/912,673, filed Oct. 26, 2007, and entitled "Double Decker Detector for Spectral CT," the entirety of which is incorporated herein by reference. In a variation, the radiation sensitive detector array 110 includes a direct conversion detector (e.g., CdTe, CdZnTe, etc.).

A reconstructor 112 reconstructs the signals output by the detector array 110. This may include decomposing the signal into various energy dependent components. An example decomposition approach is described in application serial number PCT/IB2007/055105, filed on Dec. 14, 2007, filed on Dec. 20, 2006, which is incorporated in its entirety herein by reference. The reconstructor 112 reconstructs the energy dependent components, generating one or more images corresponding to one or more different energies. The reconstructor 112 may also combine the energy dependent components, generating non-spectral image data.

A subject support 113, such as a couch, supports an object or subject in the examination region. A general purpose computer serves as an operator console 114. The console 114 includes a human readable output device such as a monitor or display and an input device such as a keyboard and mouse. Software resident on the console 114 allows the operator to interact with the scanner 100 via a graphical user interface (GUI) or otherwise. This interaction may include selecting a spectral imaging protocal or a non-spectral imaging protocal, initiating scanning, etc.

A computing system 116, such as computers, includes input/output (I/O) 118 that facilitates communication with the imaging system 100, an output device(s) 120 such as a display monitor, a filmer, etc., and an input device(s) 122 such as a mouse, keyboard, etc. The computing system 116 further includes at least one processor 124 (e.g., a central processing unit or CPU, a microprocessor, or the like) and a computer readable storage medium 126 (which excludes transitory medium), such as physical memory and/or other non-transitory memory. The computer readable storage medium 126 stores computer readable instructions 128 and data 130. The at least one processor 124 executes the computer readable instructions 128. The at least one processor 126 can also execute computer readable instructions carried by a signal, carrier wave, and other transitory (i.e., non-computer readable storage) medium.

The computer readable instructions 128, in the illustrated embodiment, include at least a bone segmentation algorithm 132. As described in greater detail below, the bone segmentation algorithm 132 includes removal of spectral noise from spectral image data with an approach that preserves the underlying object structure and spectral information, followed by extraction of a set of features for each voxel in the dataset, determination of a probability of each voxel belonging to bone structure, segmentation of global structure of bone of the image data, and optional visual refinement of the segmentated global structure. The spectral image data includes at least a first set of image data corresponding to a first energy and second set of image data corresponding to a second different energy.

In the illustrated embodiment, the spectral image data is obtained from the imaging system 100. In a variation, the spectral image data is obtained from a different imaging system. In another variation, the spectral image data is obtained from a data repository such as a picture archiving and communication system (PACS), a radiology information system (RIS), a hospital information system (HIS), an electronic medical record (EMR), a database, a server, an imaging system, a computer and/or other data repository. With this embodiment, the spectral image data is generated with the imaging system 100, different imaging system, etc. The data can be transferred to the computing system 116 via Digital Imaging and Communications in Medicine (DICOM), Health Level 7 (HL7), and/or other formats.

FIG. 2 shows an example of the bone segmentation algorithm 132.

The bone segmentation algorithm 132 includes a spectral noise remover 202. The spectral noise remover 202 removes noise and artifacts from the image data while preserving the underlying object structure and spectral information. An example of the spectral noise remover 202 is schematically illustrated in FIG. 3.

In FIG. 3, a reference structure selector 302 selects a local reference dataset. The local reference dataset is selected to provide a reference dataset that can be used to derive underlying local object structures. A noise modeler 304 analyzes the selected reference dataset and models its noise pattern.

A noise remover 306 removes the noise. This includes estimating the underlying local structure from the reference dataset. This further includes propagating the estimated structure to the target dataset and utilizing it as additional constraints for a restoration. Some of the removed texture and/or noise can be added back. This provides control over the final image appearance. Another example of spectral noise removal is described in patent application Ser. No. 60/767,300, filed on Feb. 21, 2013, and entitled "STRUCTURE PROPAGATION RESTORATION FOR SPECTRAL CT," which is incorporated herein by reference in its entirety.

In general, in dual energy image data, each of a specific energy image is usually based on roughly half of the radiation dose of a corresponding non-spectral conventional scan. In addition, the estimate of the material decomposition is based on projections between two vectors that the angle between them is narrow. The combination of these two factors, i.e., large noise and narrow angle, amplifies significantly the noise in the estimated material decomposition. The noise remover 306 reduces this noise.

Returning to FIG. 2, the bone segmentation algorithm 132 further includes a feature extractor 204. The feature extractor 204 extracts a set of features for each voxel in the dataset. The features are based on the local spectral and the local structure/geometry around the voxel. The set of features characterize the voxel and enable subsequent classification.

Examples of suitable features include, but are not limited to: 1) a Hounsfield unit (HU) of the lower energy image data, where the low energy image data can be either lower kVp image data or lower keV virtual monochromatic image data; 2) an HU of the higher energy image data, where higher energy image data can be either higher kVp image data or higher keV virtual monochromatic image data; 3) a Difference of Gaussians (DOG) of the lower energy image data; 4) a DOG of the higher energy image data, and a "surfaceness" metric.

The lower and higher energy image data correspond, in this example, to the two energies in a dual-energy scan. The DOG of the lower energy image data represents, for example, iodine, and the higher energy image data represents, for example, calcium. The DOGs may provide an enhancement where there is a small amount of iodine or calcium in the image data. The "surfaceness" metric, for example, indicates how well the local structure fit to structure of the surface. An example approach for computing the "surfaceness" metric is shown in EQUATION 1:

$$\text{Surfaceness} = \frac{|\lambda_1||\lambda_3|}{\lambda_2^2}, \quad \text{EQUATION 1}$$

where $|\lambda_1| \geq |\lambda_2| \geq |\lambda_3|$ are the eigenvalues of the local structure tensor. The set of features in this example represents a vector of features.

The bone segmentation algorithm 132 further includes a voxel probability determiner 206. The voxel probability determiner 206 determines a probability of each voxel belonging to bone structure. The voxel probability determiner 206 determines the probability based on the extracted features, for example, the local spectral and the local structure around the voxel. The utilization of both spectral and structural/geometrical properties within a unified estimator can enhance the performance of the estimator.

An example of determining a probability is shown in EQUATION 2:

$$P(V_i \in \text{Bone} | X_i) = \frac{1}{1+e^{-\beta \cdot X_i}}, \quad \text{EQUATION 2}$$

which is a multivariate logistic regression approach, which determines the probability that voxel, $V_i$, belongs to a bone structure, where $X_i$ is the vector of features for voxel $V_i$, $X_0$ is an additional explanatory pseudo-variable with a fixed value of 1, and $\beta$ is a parameter vector of the logistic regression.

The bone segmentation algorithm 132 further includes a segmentor 208. The segmentor 208 extracts the global structure of bone of the image data. In one instance, the segmentor 208 applies a segmentation model over the results of the voxel probability determiner 206. The model, for example, is a globally convex segmentation model. The globally convex segmentation model can be used to obtain reliable and robust results based on the fast numerical method.

An example of a suitable segmentation model is shown in EQUATION 3:

$$\underset{0 \leq s \leq 1}{\text{Min}} \int |\nabla s| + \lambda((c_1-p)^2 - (c_2-p)^2)s, \quad \text{EQUATION '3}$$

where the segmentation, s, is obtained by optimization (e.g., minimization in this example), $\int |\nabla s|$ represents total variation, is a parameter that controls the strength of the regularization, p is local estimator results and the rest of the parameters are segmentation parameters. In one non-limiting instance, $c_1$ is set to a numerical value of one (1) and $c_2$ is set to a numerical value of zero (0). In a variation, at least one of $c_1$ or $c_2$ is a different value.

Other suitable segmentation algorithms are described in Shi et al., "Normalized cuts and image segmentation," Pattern Analysis and Machine Intelligence, IEEE Transactions on 22.8 (2000): 888-905, Goldstein et al., "Geometric applications of the split Bregman method: segmentation and surface reconstruction," Journal of Scientific Computing 45.1-3 (2010): 272-293, and/or other segmentation algorithms.

A refiner 210 visually refines the extracted global structure of the bone. For example, bone consists of different types of tissue—cortical (compact) bone and trabecular (porous) bone. As such, the probability for all the bone in the image data may not be the same. As a consequence, the extracted bone may have holes or darker regions for voxels where the probability is lower than the voxels representing other regions of the bone. The refiner 210 fills in the holes, producing a more uniform representation of the extracted bone. In one instance, this results in an intensity of trabecular bone in the extracted bone being approximately a same intensity as an intensity of cortical bone in the extracted bone.

FIG. 4 illustrate an example method for segmenting bone structure from image data.

It is to be appreciated that the ordering of the acts in the method is not limiting. As such, other orderings are contemplated herein. In addition, one or more acts may be omitted and/or one or more additional acts may be included.

At 402, spectral image data, including a plurality of images corresponding to different energy bins, is obtained. As discussed herein, in one non-limiting instance the spectral image data can be generated by a multi-source imaging system, fast kVp switching, and/or a multi-layer detector. Alternatively, the input images can include virtually monochromatic images.

At 404, the spectral image data is de-noised. As described herein, in one non-limiting instance this includes employing an algorithm that removes noise and artifacts from the spectral image data while preserving the underlying object structure and spectral information.

At 406, a set of features is extracted for each voxel in the dataset. As described herein, in one non-limiting instance this includes extracting features based on the local spectral and the local structure/geometry around the voxel that characterize the voxel for classification.

At 408, a probability of each voxel belonging to a bone structure is estimated. As described herein, in one non-limiting instance this includes estimating the probability based on the extracted features, i.e., local spectral and local structure around the voxel.

At 410, global structure of bone is extracted from the image data. As described herein, in one non-limiting instance this includes applying a segmentation model over the probability.

At 412, the extracted global structure of bone is visually refined. As described above, this may include filling in darker regions corresponding to trabecular bone.

At 414, an image data set of the segmented or extracted global structure of bone is output. This may include visually displaying the segmented bone and/or conveying the segmented bone to another device. Again, this algorithm provides a fast, automatic and robust bone segmentation algorithm for spectral CT.

The above provides a fast, automatic and robust bone segmentation algorithm for spectral CT. The algorithm is well suited for applications such as trauma, vessel and orthopedic applications. The algorithm also can be utilized to enhance spectral results such as iodine map, virtual non-contrasted (VNC) (and therefore facilitate reducing radiation), enhancement of perfusion analysis (based on iodine map), etc. Furthermore, the algorithm can be utilized also in the image reconstruction chain, e.g., enhance beam hardening correction and virtual monochromatic image reconstruction.

The above acts may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for segmenting bone in spectral image data, which includes at least a first set of image data corresponding to a first energy and second set of image data corresponding to a second different energy, the method comprising:
    obtaining the spectral image data;
    extracting a set of features for each voxel in spectral image data, wherein the set of features are based on local spectral data and a structure represented in an adjacent voxel;
    determining, for each voxel, a probability that each voxel represents bone structure based on the set of features; and
    extracting bone structure from the spectral image data based on the probabilities.

2. The method of claim 1, further comprising:
    visually refining the extracted bone so that an intensity of trabecular bone in the extracted bone is approximately a same intensity as an intensity of cortical bone in the extracted bone.

3. The method of claim 1, wherein the extracted bone structure is at least one of visually displayed, applied as a mask for other image data, employed to enhance an iodine map or virtual non-contrasted image data, beam hardening correction, and virtual monochromatic image reconstruction.

4. The method of claim 1, further comprising:
    de-noising, prior to extracting the set of features, the spectral image data, wherein the set of features is extracted from the de-noised spectral image data.

5. The method of claim 1, wherein the first energy is lower than the second energy, and the set of features includes at least a Hounsfield unit of the first energy image data; a Hounsfield unit of the second energy image data; a difference of Gaussians of the first energy image data; a difference of Gaussians of the second energy image data, and a surfaceness metric.

6. The method of claim 5, further comprising:
    computing the surfaceness metric based on:

$$\frac{|\lambda_1||\lambda_3|}{\lambda_2^2},$$

where $|\lambda_1| \geq |\lambda_2| \geq |\lambda_3|$ are eigenvalues of a local structure tensor.

7. The method of claim 1, wherein the probability is determined based on the extracted features.

8. The method of claim 1, further comprising:
    computing the probability based on:

$$P(V_i \in \text{Bone} | X_i) = \frac{1}{1 + e^{-\beta \cdot X_i}},$$

where $V_i$ is a probability that a voxel belongs to a bone structure, $X_i$ is a vector of features for voxel $V_i$, $X_0$ is a pseudo-variable with a fixed value of 1, and $\beta$ is a parameter vector of a logistic regression.

9. The method of claim 1, wherein extracting the bone structure includes applying a segmentation model over the probabilities.

10. The method of claim 9, wherein the segmentation model includes a globally convex segmentation model.

11. The method of claim 1, wherein the segmentation is based on:

$$\min_{0 \leq s \leq 1} \int |\nabla s| + \lambda((c_1 - p)^2 - (c_2 - p)^2)s,$$

where s represents the segmentation, $\int |\nabla s|$ represents total variation, $\lambda$ is a parameter that controls the strength of the regularization, p is the probability, $c_1$ is set to a numerical value of one (1), and $c_2$ is set to a numerical value of zero (0).

12. A computing system, comprising:
    computer readable storage medium that stores a bone segmentation algorithm; and
    a computer processor that executes the bone segmentation algorithm, which causes the computer processor to:
    extract bone structure from spectral image data based on a probability that each voxel in the spectral image data represents bone structure;
    de-noise the spectral image data;

extract a set of features for each voxel in de-noised spectral image data, wherein the set features are based on local spectral data and a structure represented in an adjacent voxel;

determines, for each voxel, the probability based on the set of features; and extract the bone structure from the spectral image data based on the probabilities.

13. The computing system of claim 12, wherein the computer processor: visually refines the extracted bone.

14. The computing system of claim 12, wherein the set of features includes at least a Hounsfield unit of lower energy image data; a Hounsfield unit of higher energy image data; a difference of Gaussians of the lower energy image data; a difference of Gaussians of the higher energy image data, and a surfaceness metric.

15. The computing system of claim 14, wherein the surfaceness metric indicates how well local structure fit to structure of a surface.

16. The computing system of claim 12, wherein the computer processor at least one of visually displays the extracted bone structure or one or more of applies the extracted bone structure as a mask for other image data, to enhance an iodine map or virtual non-contrasted image data, in a beam hardening correction, or with a virtual monochromatic image reconstruction.

17. A computer readable storage medium encoded with one or more computer executable instructions, which, when executed by a processor of a computing system, causes the processor to:

obtain spectral image data, wherein the spectral image data includes at least a first set of image data corresponding to a first energy and second set of image data corresponding to a second different energy;

de-noise the spectral image data;

extract a set of features for each voxel in de-noised spectral image data, wherein the set of features are based on local spectral data and a structure represented in an adjacent voxel;

determine, for each voxel, a probability that each voxel represents bone structure based on the set of features;

extract bone structure from the spectral image data based on the probabilities; and visually refine the extracted bone.

* * * * *